(12) United States Patent
De Canniere et al.

(10) Patent No.: US 7,871,374 B2
(45) Date of Patent: Jan. 18, 2011

(54) SURGICAL RETRACTOR

(75) Inventors: Bernard De Canniere, Brussels (BE); Michel Joie, Ernage (BE)

(73) Assignee: St. Jude Medical Systems AB, Uppsala (SE)

( * ) Notice: Subject to any disclaimer, the term of this patent is extended or adjusted under 35 U.S.C. 154(b) by 330 days.

(21) Appl. No.: 11/372,520

(22) Filed: Mar. 10, 2006

(65) Prior Publication Data

US 2007/0038032 A1    Feb. 15, 2007

(51) Int. Cl.
*A61B 1/32* (2006.01)
(52) U.S. Cl. ..................... 600/208; 600/210
(58) Field of Classification Search ........... 600/210, 600/190, 193, 196, 201, 204, 206, 208, 215, 600/219; 141/297, 340; 220/666, 677, 680
See application file for complete search history.

(56) References Cited

U.S. PATENT DOCUMENTS

| | | | |
|---|---|---|---|
| 2,605,582 A * | 8/1952 | Allen | ........................ 43/100 |
| 5,342,385 A | 8/1994 | Norelli et al. | |
| 6,083,155 A | 7/2000 | Trese | |
| 2003/0153927 A1* | 8/2003 | DiPoto et al. | ............... 606/108 |
| 2003/0191371 A1 | 10/2003 | Smith et al. | |
| 2004/0116954 A1 | 6/2004 | Pagliuca et al. | |

FOREIGN PATENT DOCUMENTS

WO    WO 2004/021899 A    3/2004

* cited by examiner

*Primary Examiner*—Cris L Rodriguez
*Assistant Examiner*—Hao D Mai
(74) *Attorney, Agent, or Firm*—Townsend and Townsend and Crew LLP

(57) ABSTRACT

A Surgical retractor, designed in particular for minimally invasive operations, consisting essentially of an elastic plate rolled up about an axis so as to form the side wall of a substantially truncated cone shape, the narrowest cross section of the truncated cone constituting the distal part of this retractor, when the retractor is in place, and delimiting an operating field, the widest cross section of the truncated cone forming the proximal part, through which instruments can be introduced, said plate being able to be rolled up into a substantially cylindrical shape with a diameter smaller than or equal to the narrowest cross section of its truncated cone shape.

11 Claims, 6 Drawing Sheets

SURGICAL RETRACTOR

FIELD OF THE INVENTION

The invention relates to surgical retractors, in particular to retractors used in the field of minimally invasive surgery, for example for operations in the cardiac field.

Retractors are instruments intended to clear the operating field by spreading apart the edges of an incision or of a natural orifice. Thus, in conventional cardiac surgery, the operating surgeon has a relatively wide operating field, resulting from the fact that a sternotomy has been performed. The situation is very different in the case of minimally invasive surgery: the access routes are small incisions made in particular between the ribs; the operating surgeon does not generally have a direct view of the operating field, but instead has a view through an endoscope; the instruments have to be operated remotely within a very small space and are therefore very different to handle.

BACKGROUND OF THE INVENTION

Conventional retractors are known in this field which have the form of spatulate hooks.

This type of retractor is also used in minimally invasive surgery.

In the case of intrathoracic surgery performed without a sternotomy, it is necessary to exert traction from the outside, either by an operating surgeon holding the retractor via a handle, or by fastening it to the surrounding tissues, which includes the rib cage, or by threads passing through the rib cage.

There are also retractors that can be described as peripheral retractors, which are used for example in eye surgery (see U.S. Pat. No. 6,083,155).

However, this type of retractor can be used only in operations in which there is no problem of access and in which the operating field is not deep. Pneumatic retractors formed by an inflatable cuff are also known from U.S. Pat. No. 5,342,385. This type of retractor, which is of considerable size, poses problems of deflation if torn by a cutting instrument.

Retractors specifically designed for spinal surgery are also known from US 2004/116954 and from WO 2004/021899. These retractors comprise, mounted at the end of a cylindrical tube, a truncated cone part in the shape of a funnel (widening toward the distal part). This is a relatively complex device which has to be deployed with force. Moreover, this type of retractor does not permit direct viewing of the operating field, and the<<keyhole>>view produced is advantageous only if the eye of the camera is near the incision, which is not always the case.

SUMMARY OF THE INVENTION

It has been sought to produce a rectractor of small size which is easy to introduce into the inside of a patient's body, requires a reduced number of steps for putting it into place, and permits easy access and also a clear view of an operating field, either directly or by way of an endoscope.

The subject of the invention is a surgical retractor consisting essentially of an elastic plate rolled up about an axis so as to form the side wall of a substantially truncated cone shape, the narrowest cross section of the truncated cone constituting the distal part of this retractor when the retractor is in place, and delimiting an operating field, the widest cross section of the truncated cone forming the proximal part, through which instruments can be introduced. Said plate is able to be rolled up into a substantially cylindrical shape with a diameter smaller than or equal to the narrowest cross section of its truncated cone shape.

The apparently very simple design of this retractor is the result of an extensive study of the ergonomic requirements of surgeons in the field of minimally invasive surgery. In particular, the maneuvres required for putting it into place afford a considerable saving in terms of time. In addition, the reduced stress that it exerts on the wall of. the incised organs means that it is especially indicated for operations on hollow organs such as the heart, the intestines, etc. Moreover, even if the incision is of a small size, the operating surgeon has, compared to the prior art, twice the view of the operating field, that is to say by direct viewing through the incisions combined with a view by way of an endoscope.

According to an advantageous embodiment, the retractor comprises connecting means that are able to keep the side wall of the truncated cone rolled up at a defined diameter. These connecting means can in particular comprise a button and a buttonhole. The advantage of these elements lies in avoiding distortion at the moment of deployment or during the course of the operation.

According to one embodiment, in the absence of stress, the elastic plate that constitutes the side wall of the truncated cone shape spontaneously adopts a substantially flat shape.

According to another embodiment, in the absence of stress, the elastic plate that constitutes the side wall of the truncated cone shape spontaneously adopts a truncated cone shape.

The plate preferably has a shape substantially in the form of a truncated crescent, the inner curve of this crescent, in the form of an arc of a circle, having a length corresponding to the maximum perimeter of the narrowest cross section of the truncated cone, and, instead of the horns of the crescent, it comprises two sides which are substantially parallel to one another, their length corresponding to the height of the truncated cone.

The surgical retractor of the invention preferably comprises protuberances arranged on the flanks of the wall of the truncated cone.

It advantageously comprises, at the proximal end, grip means facilitating its manipulation.

These grip means are preferably able to cooperate with gripper means mounted on the end of positioning tools of elongate shape, said positioning tools allowing the plate to be rolled up and to be maintained in the rolled-up state.

According to an advantageous embodiment, these positioning tools comprise connecting means with which it is possible to secure them together so as to facilitate their manipulation, particularly with the retractor maintained in the rolled-up position.

The inner face of the surgical retractor according to the invention is preferably transparent. In this case, according to an advantageous embodiment, the outer face of the plate comprises conductive elements that are able to be connected to a generator so as to produce localized tissue necrosis, such as that produced in the elimination of atrial fibrillation.

The plate can also be made of a frosted material, which can be metal or plastic, in order to avoid interference from reflections during use.

The proximal end of the plate advantageously comprises fixation points for means for holding the retractor in the course of an operation. These holding means can, for example, be a support formed by suture threads, etc.

BRIEF DESCRIPTION OF THE FIGURES

These features, and other features of the invention, will become clear from the following detailed description of particular embodiments of the invention, reference being made to the figures in the drawings, in which.

The figures are not drawn to scale. Generally, similar elements are designated by similar reference labels in the figures. The present invention will be described in the context of specific embodiments that have been chosen as non-limiting illustrations.

DETAILED DESCRIPTION OF THE FIGURES

Figure 1:
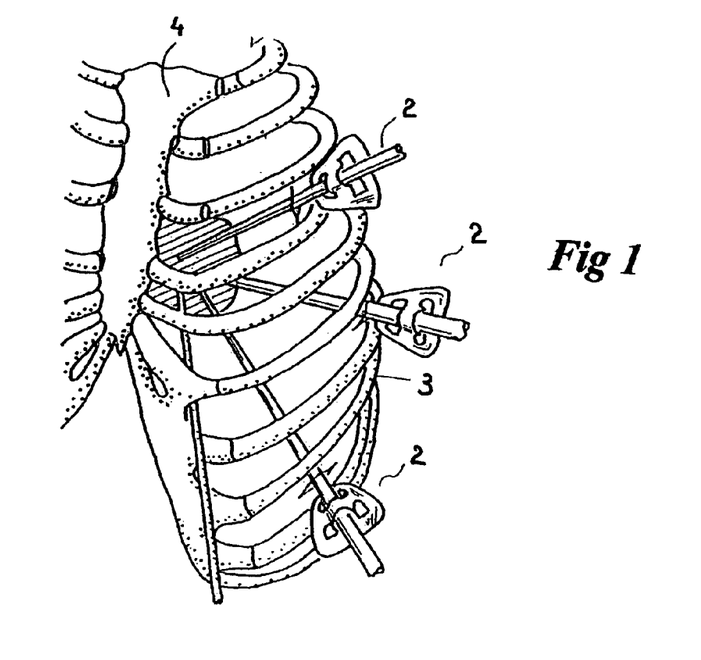
FIG. 1 is a schematic and cut-away perspective view of a standard intrathoracic operation performed by a minimally invasive technique.

FIG. 1 shows the conditions in which minimally invasive intrathoracic surgery is performed: the instruments 2 are introduced inside the thorax via small incisions, without cutting the ribs 3 or sternum 4.

Figure 2:
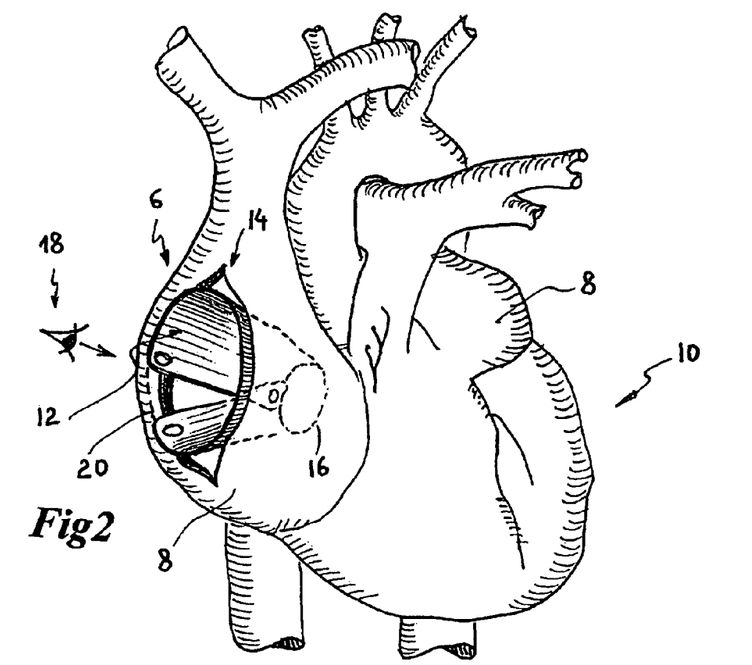
FIG. 2 is a perspective view of a retractor according to the invention positioned in an atrium of the heart.

FIG. 2 shows the retractor 6 of the invention positioned for an operation on an atrium 8 of the heart. As the walls of the heart 10 are relatively thin and have little muscle in the area of the atrium 8, it would be awkward to place conventional retractors there which are anchored to the rib cage 3. As will be seen, the retractor 6 basically comprises a plate 12, made of an elastic material, rolled up so as to form the side wall of a truncated cone. The distal part of this truncated cone is driven through an incision 14 into the interior of the atrium 8. The narrowest cross section 16 of the truncated cone thus delimits the operating field, while the conicity of the wall provides a clear zone for movement of the surgical instruments and for the viewing field of the operating surgeon, which in this case corresponds to the field covered by an endoscope 18 placed near the axis of the truncated cone, in the area of its widest cross section 20. To maximize the stereoscopic vision that the operating surgeon may have of the operating field, it is important to widely retract the tissues freed by the incision.

Figure 3:
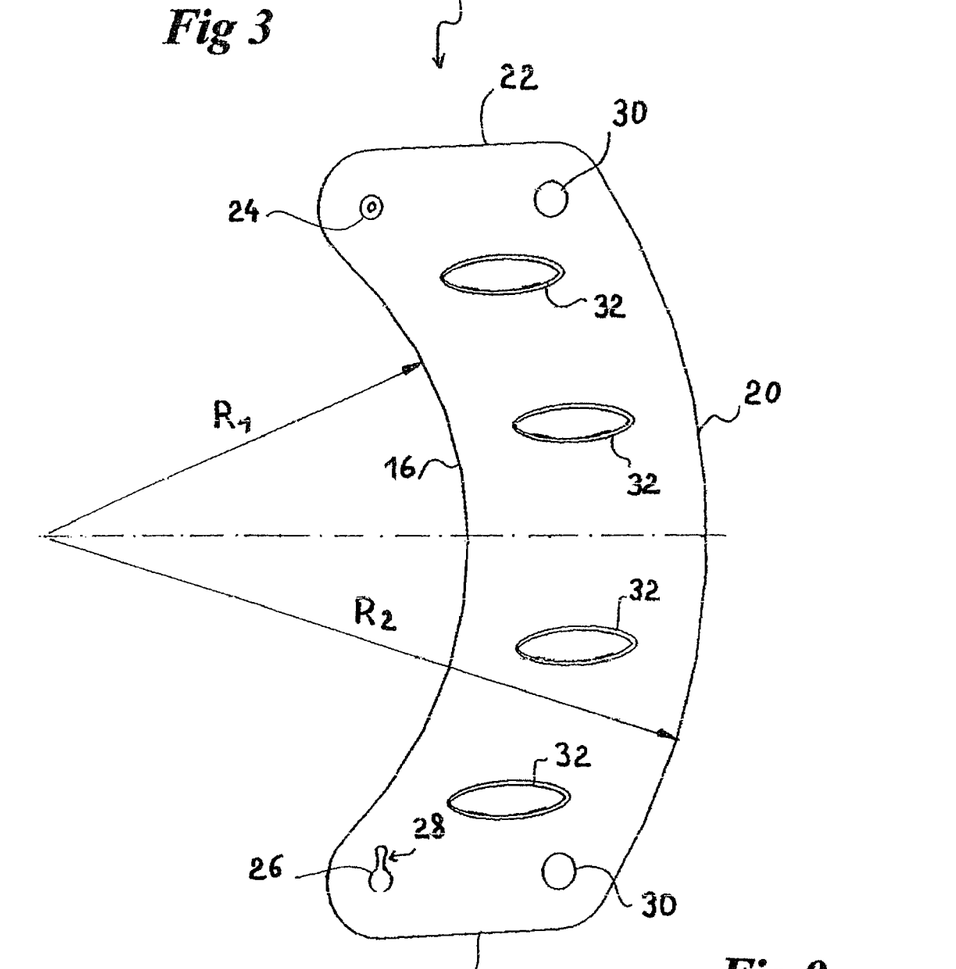
FIG. 3 is a plan view of a retractor according to the invention spread out flat.

FIG. 3 shows one embodiment of the retractor 6. In this embodiment, the elastic plate 12, in the absence of stress, adopts a substantially flat shape. Its shape as a crescent, with the two horns cut away, corresponds substantially to the side wall of a truncated cone and comprises two sides in the shape of arcs of a circle: an inner side 16 with a length corresponding to that of the narrowest cross section of a truncated cone and with radius R1, and an outer side 20 with radius R2 corresponding partially to the circumference of the large cross section of the truncated cone. As can be seen from FIG. 3, the large cross section 20 has part of its circumference cut off by two substantially parallel sides 22 issuing from the ends of the side 16.

At the side corresponding to the narrowest cross section of the truncated cone, the plate 12 is provided with connecting means 24, 26 which cooperate with one another to maintain the retractor in the curved shape when they are engaged in one another.

Figure 4:
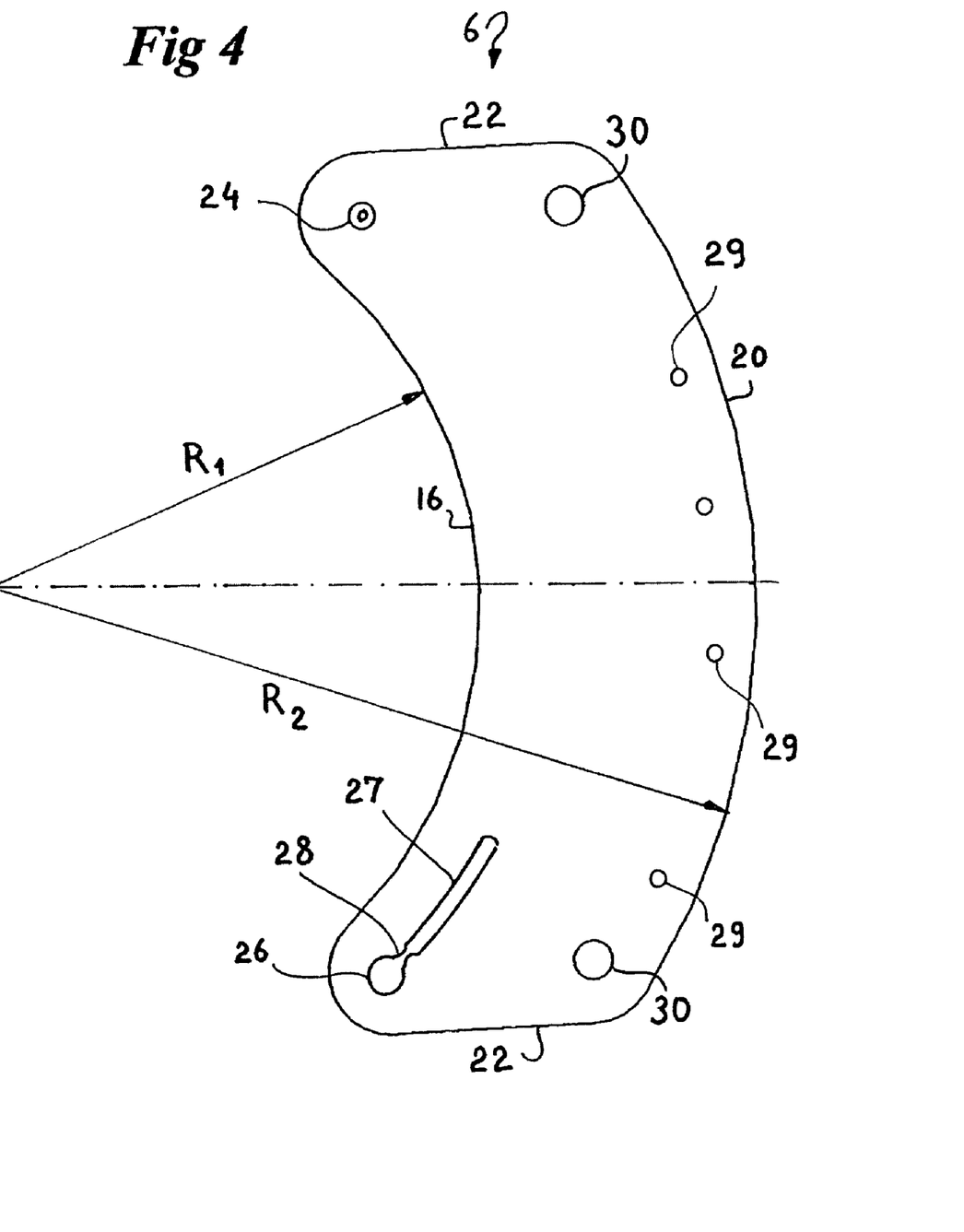
FIG. 4 is a plan view of another embodiment of a retractor according to the invention spread out flat.

As shown in FIG. 3, these connecting means are a button 24 and a buttonhole 26 with catch 28, but it goes without saying that other embodiments (clips, snap fasteners, etc.) may be used. Several points of connection may be provided, this making it possible to vary the nominal diameter of the retractor depending on the size of the organ to be operated on, or, as is shown in FIG. 4, making it possible to extend the buttonhole so as to obtain a variable cross section.

A series of perforations are formed along the proximal face of the plate. They form anchoring points 29 with which it is possible, if necessary, to tie the retractor to the surrounding tissues.

Grip means 30, in this case openings 30, can be seen near both ends of the side corresponding to the circumference of the large cross section of the truncated cone. Their role will be explained further below.

Protuberances 32, in this case arranged longitudinally, protrude along the length of the plate. They have a secondary role of stiffeners, but their main function is to avoid adherence of the inner walls of the incised organ 14 against the continuous surface of the plate 12. These protuberances can be lengthened and can form fold lines which, if necessary, transform the operating field into a polygonal surface.

FIG. 4 shows another embodiment of the retractor according to the invention. In this embodiment, a very long buttonhole 27 is used, also provided with catch means 28, permitting automatic adaptation of the diameter to the length of the incision and to the diameter of the distal operating field. In addition, it is thereby possible to considerably reduce the diameter of the retractor in the rolled-up state.

Figure 5:
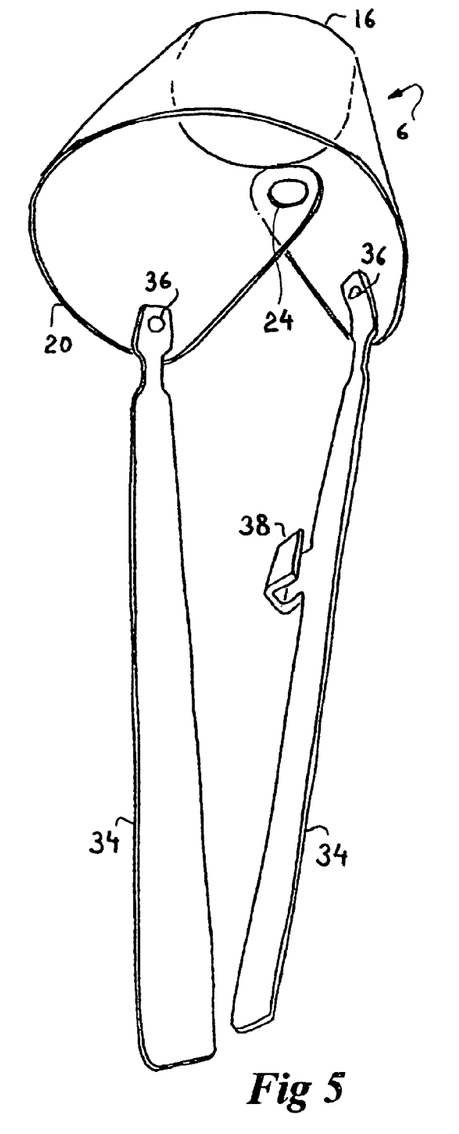
FIGS. 5 and 6 are perspective views of instruments for manipulating a retractor according to the invention, keeping the retractor respectively deployed and rolled up in a compact form for introduction.
Figure 6:
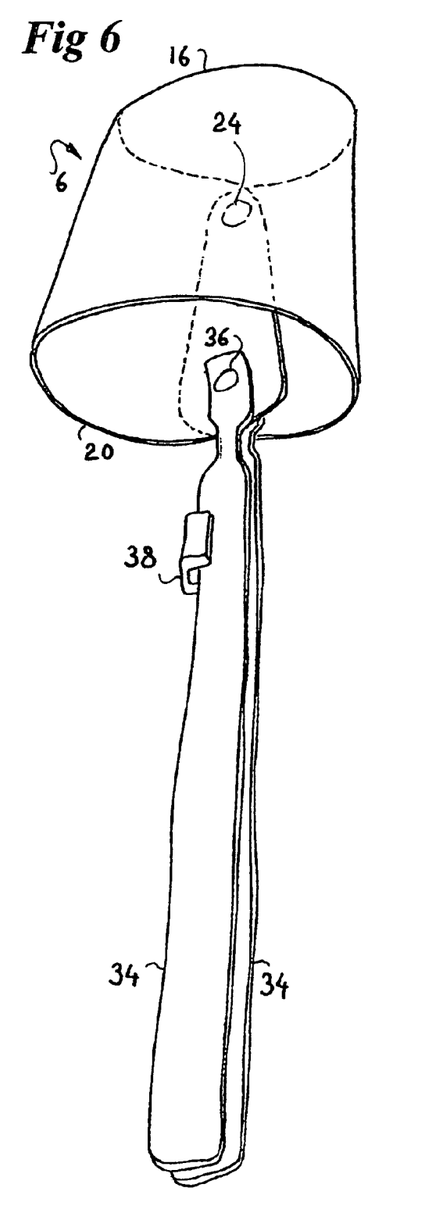

FIGS. 5 and 6 permit a better understanding of the role of the grip means 30 and of the way in which the retractor is fitted in place. To insert the retractor 6 inside the rib cage 3, 4, the operating surgeon has two positioning instruments 34 of elongate shape. Each of these instruments is provided, at its distal end, with gripper means 36 (in this case a button-shaped head 36) that are able to cooperate with the grip means 30 of the retractor.

By manipulating the two instruments 34, the operating surgeon is able to roll the plate 12 up (see FIG. 4). The roll thus formed, of small diameter, can easily be inserted into the thorax 3, 4 through an incision and positioned in the atrium 8. The instruments 34 are specifically designed to be easily bent and therefore adapt to different angles of intervention.

To avoid the plate 12 accidentally unrolling, and to permit their manipulation by just one hand, the positioning tools 34 are provided with a securing clip 38. The presence of this securing clip 38 facilitates the work of the operating team, as the retractor can be passed from hand to hand during the operation without risk of its unrolling, thus saving precious time for the surgeon and the patient.

As soon as the positioning tools 34 are disconnected, the inherent elasticity of the plate 12 forces the retractor to open out and adopt the required truncated cone shape.

Figure 7:
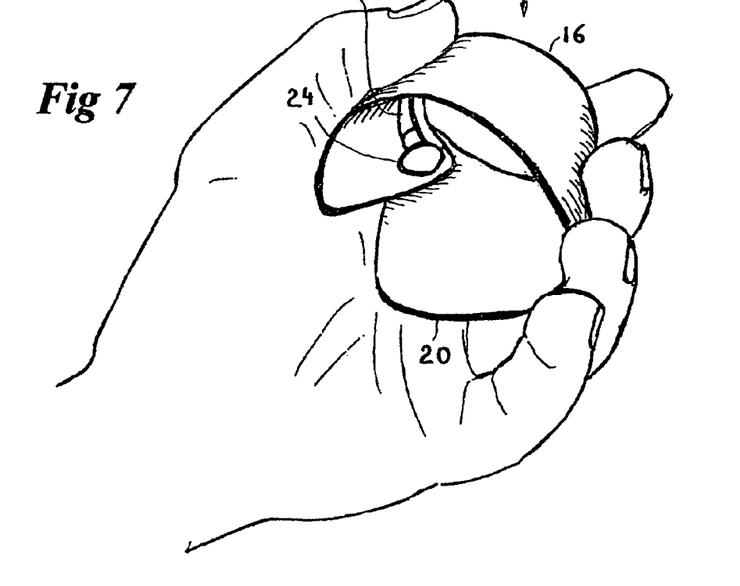
FIGS. 7, 8 and 9 are perspective views of the retractor from FIG. 4 at different stages of its manipulation.
Figure 8:
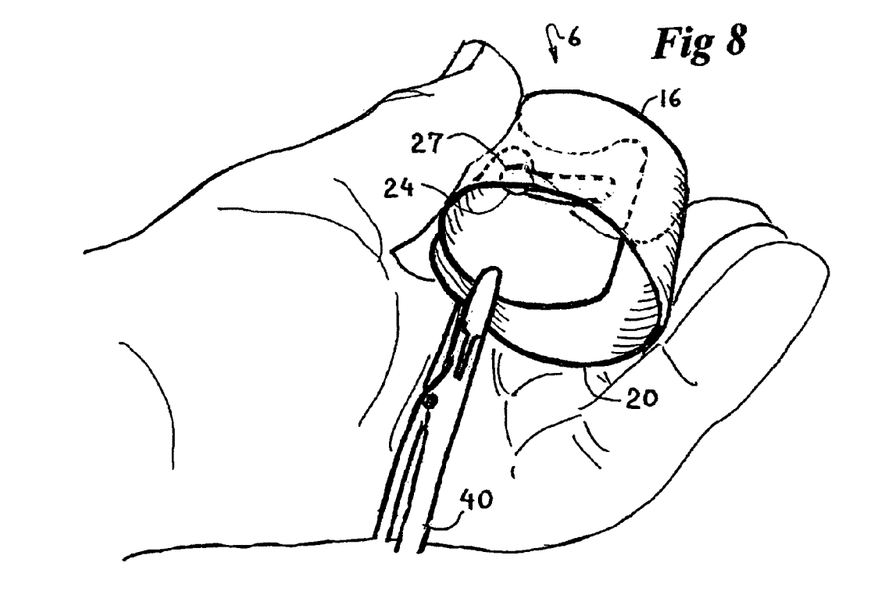
Figure 9:
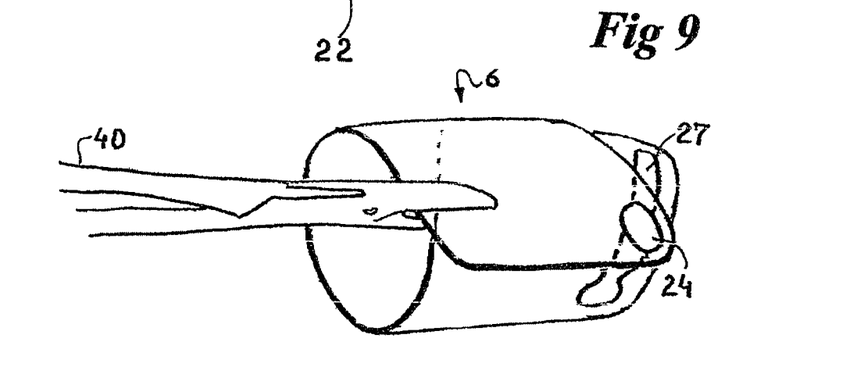

FIGS. 7, 8 and 9 show another way of introducing the retractor into place. Rather than using the positioning instruments 34 described above, the operating surgeon in this case uses conventional locking tweezers (or forceps) 40.

In FIG. 7, the operating surgeon rolls the plate up and locks the retractor in a roughly truncated cone position with the aid of the connecting means.

In FIG. 8, the operating surgeon forces the plate to roll up until he obtains a cylindrical roll of small diameter. He locks the retractor in this position with the aid of locking tweezers 40. He finally introduces the retractor into place (FIG. 9) via its distal section.

It will be noted that the substantially flat shape of the elastic plate 12 allows it to be stored flat, in a way that saves space in particular, and avoids any creep in cases where the plate is made of materials sensitive to this phenomenon. The retractor can be made of plastic materials, such as PET or PTFE, and also of a biocompatible metal such as stainless steel, titanium alloys, etc.

The retractor, like the positioning instruments 34, is offered in different standard dimensions and can either be reusable or intended to be disposed of after one use.

The advantages associated with the flat opened-out shape do not, however, mean that a retractor according to the present invention cannot, in the absence of stress, have a truncated cone shape at rest. However, even when produced in such a shape, it is preferable to provide it with connecting means, so that the pressure of the incised tissues does not cause distortion during the operation.

The retractor can be made of an opaque, translucent or transparent material. However, regardless of the material used, it is important that the inner wall reduces as far as possible any reflections that might disturb the operating surgeon. To this end, this wall may be frosted.

Figure 10:
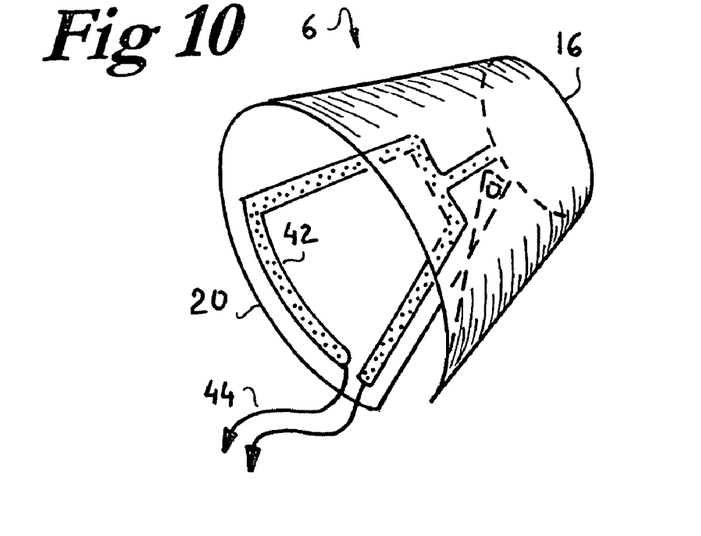
FIG. 10 is a schematic perspective view of another embodiment of the retractor.

The use of a transparent wall allows the operating surgeon to visually monitor the state of the wall. The surgical procedures are often combination procedures, and several maneuvres are often performed in succession. The repair of a mitral valve is also often accompanied by ablation of atrial fibrillation (Cox-Maze procedure). The latter involves isolating certain nerve junctions responsible for uncontrolled movements of the heart muscle. This isolation is achieved by producing necrosis of certain areas extending along a line encircling the pulmonary veins and the mitral valve. This operation is performed by locally burning the tissues by passage of an electric current or by radiofrequency, or even ultrasound or cryogenics. The electrical applications can be unipolar or bipolar. The presence of a retractor such as the one according to the invention represents-a priori an inconvenience since its wall is interposed between the zones to be treated and the tools necessary for producing the necrosis. It has therefore been proposed to place on the actual wall of the retractor the elements 42 needed for producing such necrosis, as is shown in FIG. 10.

Figure 11:
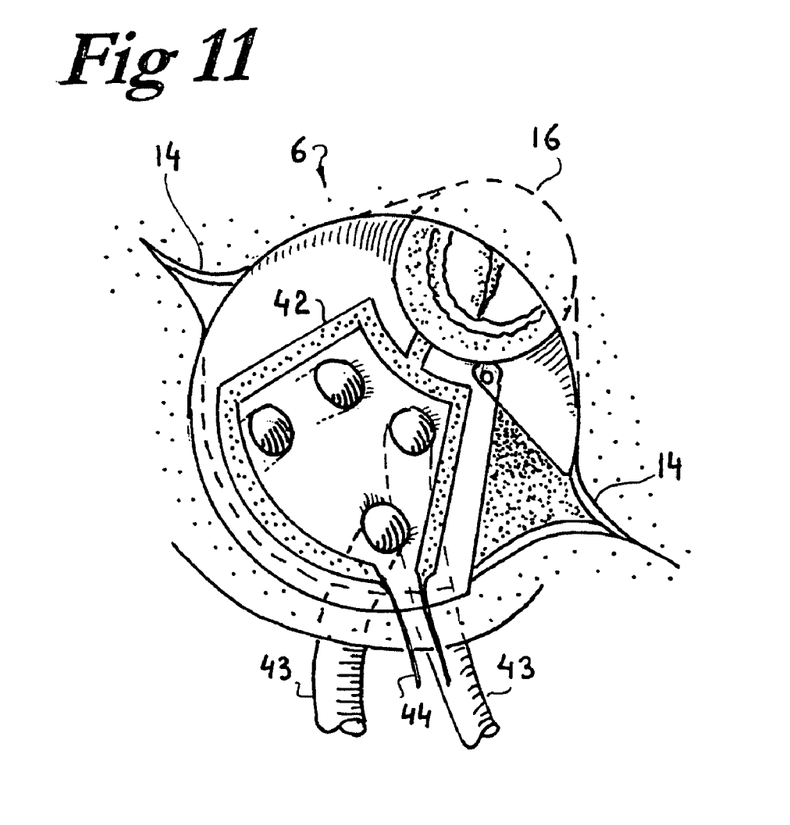
FIG. 11 is a schematic perspective view of the retractor from FIG. 10 in position in an atrium.

The retractor function is thus combined with that of a support for one or more electrodes 42 (or antennas, or even cryogenic conduits) arranged in a suitable configuration (in this case following the pathway of the lines of necrosis) and integrally joined to the wall of the retractor. Once introduced into the atrium, the retractor is positioned in such a way that the electrode or electrodes 42 are arranged in line with the zones that are to be treated (origin of the pulmonary veins 43 as shown in FIG. 11) and the required energy is administered via these electrodes or conduits 42 with the aid of an external generator, which is known to a person skilled in the art and is connected to the electrodes or to the conduit. Once this procedure has been carried out, the retractor 6 is disconnected and repositioned, if necessary, so as to fulfil strictly its role of retractor for the second procedure (such as a mitral valve repair).

In practice, the electrodes 42 are formed from wires or printed circuits coated with or embedded in a sheet of plastic material from which connecting means 44 emerge. These electrodes 42 can also be supported by a sheet of adhesive material applied to the retractor.

The different procedures involved in using the retractor 6 according to the invention can therefore be summarized as follows:
- providing a plate of elastic material that is able to adopt a substantially truncated cone shape;
- bringing said plate into its truncated cone shape;
- gripping said plate via its end of large diameter, which forms its proximal part, and rolling it up in such a way as to form a cylinder of small diameter;
- passing the retractor through the incision, with the distal part, corresponding to its narrowest diameter, towards the front;
- allowing the retractor to unroll in such a way that it readopts its truncated cone shape.

It will be obvious to a person skilled in the art that the present invention is not limited to what has been described above. The invention lies also in each of the novel characteristics and in the combination of these various characteristics.

The invention claimed is:

1. A self-expanding surgical retractor consisting essentially of an elastic plate having substantially the shape of a truncated crescent having an inner side in the shape of an arc of a circle and an outer side in the shape of an arc of a circle rolled up about an axis so as to form, in a first, deployed position, a side wall of a substantially truncated cone shape;
   the inner side of the truncated crescent forming a narrowest cross section of the truncated cone constituting a distal part of the retractor when the retractor is in place and delimiting an operating field;
   the outer side of the truncated crescent forming a widest cross section of the truncated cone forming a proximal part, through which instruments can be introduced;
   said plate, in a second, rolled up position, being rolled up into a substantially cylindrical shape with a diameter smaller than or equal to the narrowest cross section of the truncated cone shape;
   wherein the resilience of said plate is so that it forces the retractor to open out and to exert on a wall of an incised organ a reduced stress, and is sufficient to widely retract tissues freed by an incision;
   said retractor comprising a single connecting means in the form of a button and a curved elongated buttonhole placed near the inner side of the truncated crescent forming the narrowest cross section of the retractor when in its first, deployed position, said connecting means maintaining the plate in cone form in its first, deployed position;
   said retractor comprising two buttonholes placed near the outer side of the truncated crescent, forming the widest cross section of the truncated cone when in deployed position on either side of said crescent, said buttonholes being able to cooperate with button-shaped heads placed at a distal end of elongated positioning instruments for facilitating its manipulation;
   said retractor further comprising a series of perforations forming anchoring points dispersed along the outer side of the truncated crescent for allowing the widest cross section of the truncated cone when in deployed position to be tied to surrounding tissues in the course of an operation.

2. A Surgical retractor according to claim 1 wherein in the absence of stress, the elastic plate that constitutes the side wall of the truncated cone shape spontaneously adopts a substantially flat shape.

3. A Surgical retractor according to claim 1 wherein, in the absence of stress, the elastic plate that constitutes the side wall of the truncated cone shape spontaneously adopts a truncated cone shape.

4. A Surgical retractor according to claim 1, wherein the plate has a shape substantially in the form of a truncated crescent, the inner curve of this crescent, in the form of an arc of a circle, having a length corresponding to the maximum perimeter of the narrowest cross section of the truncated cone delimiting the operating field, two straight sides connecting the ends of these arcs of circles and extending substantially parallel to one another, their length corresponding to the height of the truncated cone.

5. A Surgical retractor according to claim 1, which comprises longitudinal protuberances arranged on the wall of the truncated cone.

6. A Surgical retractor according to claim 1 wherein the grip means are able to cooperate with gripper means mounted on an end of independent removable stick-shaped positioning tools of elongate shape that are connectable to the widest cross section of the truncated cone, said positioning tools further helping to bring the plate to its second, rolled up position.

7. A Surgical retractor according to claim 6 wherein the positioning tools can be secured together, with the retractor maintained in the rolled-up position.

8. A Surgical retractor according to claim 1, wherein the plate is transparent.

9. A Surgical retractor according to claim 1 wherein the plate is made out of a non-conductive material, and wherein a face of the plate facing outwardly comprises conductive elements that are able to be connected to a generator so as to produce localized tissue necrosis.

10. A method for using a surgical internal retractor comprising the following steps:

providing a plate of elastic material having substantially the shape of a truncated crescent having an inner side in the shape of an arc of a circle and an outer side in the shape of an arc of a circle, said plate being provided, near the inner side of the inner side of the truncated crescent, with interconnecting means in the shape of a button and buttonhole;

interconnecting said interconnecting means so as to bring said plate into a shape of a truncated cone;

gripping said plate via grip means placed near the outer side of the truncated crescent forming an end of the truncated cone having a largest diameter, which forms its proximal part, rolling said plate up in such a way as to form a cylinder of small diameter;

passing the retractor through an incision in a body, with the inner side of the truncated crescent, corresponding, to a narrowest diameter of the truncated cone when in deployed position, forward;

inserting the retractor into a cavity of an incised hollow organ;

allowing the retractor to unroll in such a way that it readopts its truncated cone shape, the resiliency of the plate being so that the retractor exerts on a wall of the incised organ a reduced stress, and is sufficient to widely retract tissues freed by an incision;

performing an operation on an internal organ;

rolling said plate up in such a way as to form a cylinder of small diameter;

extracting, said cylinder through the incision.

11. The method of claim 10, further comprising:

inserting the retractor into a cavity of an incised hollow organ;

wherein allowing the retractor to unroll includes allowing the retractor to unroll such that it exerts a reduced stress on the incised tissues of the hollow organ.

* * * * *